US00PP24162P2

(12) United States Plant Patent
Larsen

(10) Patent No.: US PP24,162 P2
(45) Date of Patent: Jan. 14, 2014

(54) ***OSTEOSPERMUM* PLANT NAMED 'SUNOST1101'**

(50) Latin Name: *Osteospermum ecklonis*
Varietal Denomination: Sunost1101

(75) Inventor: Bjarne Nyholm Larsen, Odense N. (DK)

(73) Assignee: Sunny Gronnegyden APS, Odense (DK)

( * ) Notice: Subject to any disclaimer, the term of this patent is extended or adjusted under 35 U.S.C. 154(b) by 71 days.

(21) Appl. No.: 13/385,836

(22) Filed: Mar. 7, 2012

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Annette Para
(74) *Attorney, Agent, or Firm* — C. A. Whealy

(57) ABSTRACT

A new and distinct cultivar of *Osteospermum* plant named 'Sunost1101', characterized by its upright, outwardly spreading and mounding plant habit; freely branching growth habit; freely flowering habit; daisy-type inflorescences with purple-colored ray florets; good garden performance and tolerance to high temperatures.

1 Drawing Sheet

Botanical designation: *Osteospermum ecklonis.*
Cultivar denomination: 'SUNOST1101'.

BACKGROUND OF THE INVENTION

The present invention relates to a new and distinct cultivar of *Osteospermum* plant, botanically known as *Osteospermum ecklonis*, and hereinafter referred to by the name 'Sunost1101'.

The new *Osteospermum* plant is a product of a planned breeding program conducted by the Inventor in Odense, Denmark. The objective of the program is to create and develop new *Osteospermum* plants with compact and uniformly mounded plant habit, freely flowering habit and attractive inflorescence coloration.

The new *Osteospermum* plant originated from a cross-pollination by the Inventor in May, 2008 of *Osteospermum ecklonis* 'Sunny Felix', disclosed in U.S. Plant Pat. No. 17,419, as the female, or seed, parent with a proprietary selection of *Osteospermum ecklonis* identified as code number 05.50.002, not patented, as the male, or pollen, parent. The new *Osteospermum* plant was discovered and selected by the Inventor as a single flowering plant within the progeny of the stated cross-pollination in a controlled greenhouse environment in Odense, Denmark in June, 2009.

Asexual reproduction of the new *Osteospermum* plant by terminal cuttings in a controlled greenhouse environment in Odense, Denmark since November, 2009 has shown that the unique features of this new *Osteospermum* plant are stable and reproduced true to type in successive generations.

SUMMARY OF THE INVENTION

Plants of the new *Osteospermum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunost1101'. These characteristics in combination distinguish 'Sunost1101' as a new and distinct *Osteospermum* plant:

1. Upright, outwardly spreading and mounding plant habit.
2. Freely branching growth habit.
3. Freely flowering habit.
4. Daisy-type inflorescences with purple-colored ray florets.
5. Good garden performance and tolerance to high temperatures.

Plants of the new *Osteospermum* differ primarily from plants of the female parent, Sunny Felix', in ray floret color as plants of 'Sunny Felix' have white-colored ray florets with a violet blue-colored spot.

Plants of the new *Osteospermum* differ slightly from plants of the male parent selection in ray floret color.

Plants of the new *Osteospermum* can be compared to plants of the *Osteospermum* 'Sunny Xandra', disclosed in U.S. Plant Pat. No. 19,634. In side-by-side comparisons conducted in Odense, Denmark, plants of the new *Osteospermum* differed from plants of 'Sunny Xandra' in the following characteristics:

1. Leaves of plants of the new *Osteospermum* were elliptic in shape whereas leaves of plants of 'Sunny Xandra' were more rounded in shape.
2. Inflorescences of plants of the new *Osteospermum* had fewer ray florets than inflorescences of plants of 'Sunny Xandra'.
3. Plants of the new *Osteospermum* and 'Sunny Xandra' differed slightly in ray floret color.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph at the bottom of the sheet comprises a side perspective view of a typical flowering plant of 'Sunost1101' grown in a container.

The photograph at the top of the sheet is a close-up view of a typical flowering plant of ' Sunost1101'.

DETAILED BOTANICAL DESCRIPTION

The aforementioned photographs, following observations and measurements describe plants grown during the summer in one-gallon containers in an outdoor nursery in Bonsall, Calif. under cultural practices which approximate those generally used in commercial *Osteospermum* production. During the production of the plants, day temperatures ranged from 27° C. to 35° C. and night temperatures ranged from 16° C. to 20° C. Plants were pinched one time and were twelve weeks old when the photographs and description were taken. In the following description, color references are made to The Royal Horticultural Society Colour Chart, 2007 Edition, except where general terms of ordinary dictionary significance are used.

Botanical classification: *Osteospermum ecklonis* 'Sunost1101'.

Parentage:

*Female, or seed, parent.*—*Osteospermum ecklonis* 'Sunny Felix', disclosed in U.S. Plant Pat. No. 17,419.

*Male, or pollen, parent.*—Proprietary selection of *Osteospermum ecklonis* identified as code number 05.50.002, not patented.

Propagation:

*Type.*—Terminal vegetative cuttings.

*Time to initiate roots, summer.*—About 12 days at 18° C.

*Time to initiate roots, winter.*—About 14 days at 18° C. to 20° C.

*Time to produce a rooted cutting, summer.*—About 20 days at 18° C. to 20° C.

*Time to produce a rooted cutting, winter.*—About 28 days at 18° C.

*Root description.*—Medium in thickness, fibrous; white in color.

*Rooting habit.*—Freely branching; medium density.

Plant description:

*Plant and growth habit.*—Upright, outwardly spreading and mounding plant habit; inflorescences positioned above and beyond the foliar plane; moderately vigorous to vigorous growth habit.

*Plant height.*—About 29.5 cm.

*Plant diameter.*—About 52 cm.

*Lateral branches.*—Quantity per plant: Freely branching habit with about eleven primary lateral branches per plant; pinching enhances branching potential. Length: About 22 cm. Diameter: About 6 mm. Internode length: About 1.1 cm to 1.5 cm. Strength: Strong. Texture: Pubescent. Color: Close to 145A.

*Foliage description.*—Arrangement: Alternate, simple. Length: About 4.4 cm. Width: About 2.3 cm. Shape: Oblanceolate. Apex: Broadly acute. Base: Attenuate. Margin: Entire to broadly dentate. Texture, upper surface: Smooth, glabrous. Texture, lower surface: Slightly pubescent; scaberulose. Venation pattern: Pinnate, arcuate. Color: Developing leaves, upper and lower surfaces: Close to 146B. Fully expanded leaves, upper surface: Close to N137A; venation, close to 146B. Fully expanded leaves, lower surface: Close to 137B; venation, close to 146B. Petiole: Length: About 6 mm. Diameter: About 5 mm. Texture, upper and lower surfaces: Smooth, glabrous. Color, upper and lower surfaces: Close to 147C.

Inflorescence description:

*Appearance.*—Daisy-type inflorescence form with oblanceolate-shaped ray florets; inflorescences terminal and axillary and positioned above and beyond the foliar plane; disc and ray florets developing acropetally on a capitulum; inflorescences face mostly upright to outwardly.

*Flowering habit.*—Freely flowering habit with about 15 inflorescences developing per plant.

*Fragrance.*—None detected.

*Flowering response.*—In southern California, plants of the new *Osteospermum* flower continuously from early spring to mid-summer; early flowering habit, plants begin flowering about six to eight weeks after planting.

*Inflorescence longevity.*—Inflorescences of plants of the new *Osteospermum* last about five days on the plant; inflorescences persistent.

*Inflorescence bud.*—Height: About 2 cm. Diameter: About 1.1 cm. Shape: Ovate to lanceolate. Color: Close to N92D.

*Inflorescence size.*—Diameter: About 5 cm. Depth (height): About 2.7 cm. Disc diameter: About 8 mm. Receptacle diameter: About 1.2 cm. Receptacle height: About 1 cm.

*Ray florets.*—Length: About 2.8 cm. Width: About 8 mm. Shape: Oblanceolate. Apex: Emarginate. Base: Attenuate. Margin: Entire. Aspect: About 45° from vertical. Texture, upper surface: Smooth, glabrous; velvety. Texture, lower surface: Smooth, glabrous; satiny. Number of ray florets per inflorescence: About 19 to 20 arranged in one to 1.5 whorls. Color: When opening, upper surface: Close to N81C. When opening, lower surface: Longitudinal stripes, close to 84D and 93C. Fully opened, upper surface: Longitudinal stripes, close to 72B and 77A; color becoming closer to N79A to N79B with development. Fully opened, lower surface: Longitudinal stripes, close to 79D and 79B.

*Disc florets.*—Shape: Tubular; apex dentate, five-pointed. Length: About 9 mm. Diameter, apex: About 2 mm. Diameter, base: About 1 mm. Number of disc florets per inflorescence: About 52. Color, immature: Apex: Close to N92A. Mid-section: Close to 93C. Base: Close to 157D. Color, mature: Apex: Close to 90B. Mid-section: Close to 93D. Base: Close to 157D.

*Phyllaries.*—Quantity per inflorescence: About 18 arranged in a single whorl. Length: About 1 cm. Width: About 2 mm. Shape: Lanceolate. Apex: Acuminate. Base: Truncate. Margin: Entire. Texture, upper surface: Smooth, glabrous. Texture, lower surface: Pubescent. Color, upper surface: Close to 146B. Color, lower surface: Close to 147B.

*Peduncles.*—Length, terminal peduncle: About 10.2 cm. Length, third peduncle: About 8.3 cm. Diameter: About 1.5 mm. Strength: Strong. Aspect, terminal peduncles: Mostly upright. Aspect, axillary peduncles: About 30° to 35° from vertical. Texture: Sparsely pubescent. Color: Close to 147B.

*Reproductive organs*.—Androecium: Present on disc florets only. Filament length: About 3 mm. Filament color: Close to NN155D. Anther shape: Oblong. Anther length: About 2 mm. Anther color: Close to N187A. Pollen amount: Moderate. Pollen color: Close to 168C. Gynoecium: Present on both ray and disc florets. Pistil length: About 6 mm. Stigma shape: Bi-parted. Stigma color: Close to 79A. Style length: About 2.5 mm. Style color: Close to 85C. Ovary color: Close to 157A.

*Seeds and fruits*.—Seed and fruit development has not been observed on plants of the new *Osteospermum*.

Disease & pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind, high temperatures of about 40° C. and to be hardy to USDA Hardiness Zone 9.

It is claimed:

1. A new and distinct *Osteospermum* plant named 'Sunost1101' as illustrated and described.

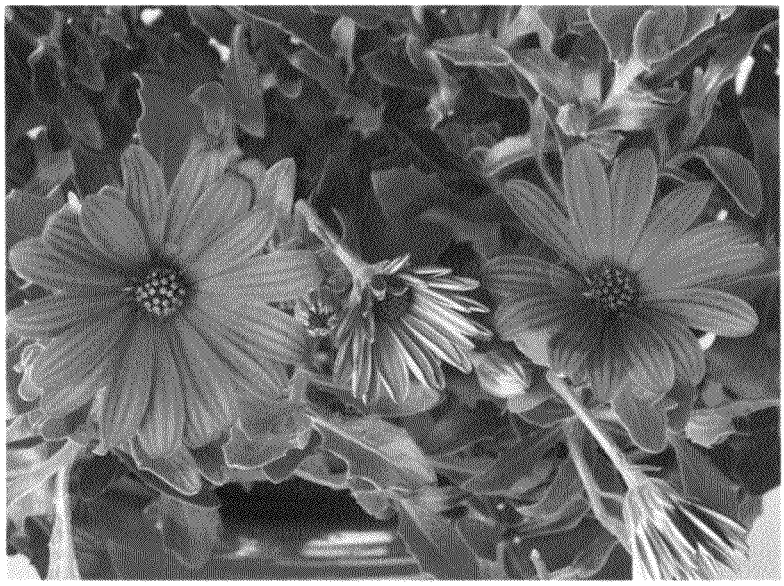
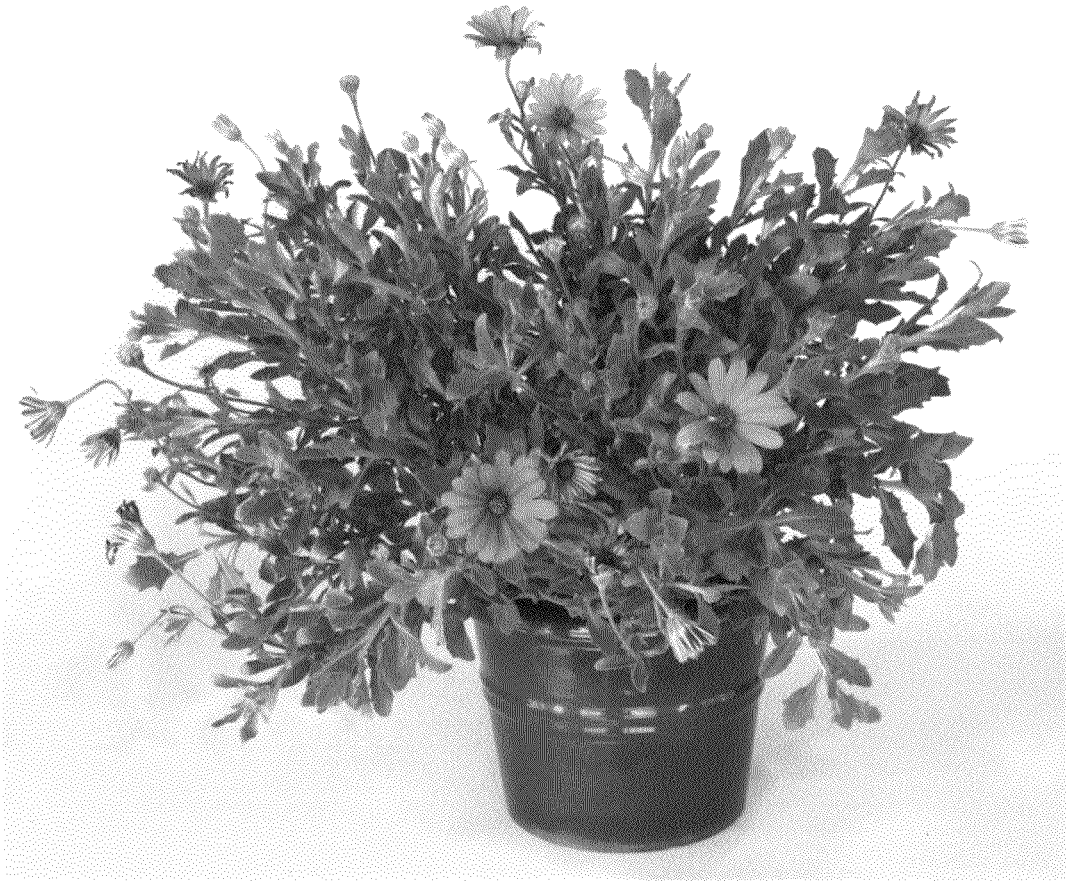

* * * * *